United States Patent
Choukroun

(10) Patent No.: US 9,628,697 B2
(45) Date of Patent: Apr. 18, 2017

(54) METHOD AND DEVICE FOR MEASURING AN INTERPUPILLARY DISTANCE

(75) Inventor: Ariel Choukroun, Toulouse (FR)

(73) Assignee: FITTINGBOX, Labege (FR)

( * ) Notice: Subject to any disclaimer, the term of this patent is extended or adjusted under 35 U.S.C. 154(b) by 1137 days.

(21) Appl. No.: 13/634,954

(22) PCT Filed: Mar. 18, 2011

(86) PCT No.: PCT/EP2011/054138
§ 371 (c)(1),
(2), (4) Date: Dec. 12, 2012

(87) PCT Pub. No.: WO2011/113936
PCT Pub. Date: Sep. 22, 2011

(65) Prior Publication Data
US 2013/0076884 A1    Mar. 28, 2013

(30) Foreign Application Priority Data
Mar. 19, 2010    (FR) ...................... 10 52001

(51) Int. Cl.
| A61B 3/00 | (2006.01) |
| A61B 3/08 | (2006.01) |
| H04N 5/232 | (2006.01) |
| A61B 3/11 | (2006.01) |
| G06K 9/00 | (2006.01) |
| G06T 7/60 | (2017.01) |
| A61B 3/14 | (2006.01) |

(52) U.S. Cl.
CPC .......... *H04N 5/23219* (2013.01); *A61B 3/111* (2013.01); *G06K 9/00604* (2013.01); *G06T 7/602* (2013.01); *G06T 2207/10016* (2013.01); *G06T 2207/30041* (2013.01)

(58) Field of Classification Search
USPC .................. 351/204, 200, 203, 205, 206
See application file for complete search history.

(56) References Cited

U.S. PATENT DOCUMENTS

2010/0128220 A1* 5/2010 Chauveau ............... 351/204

FOREIGN PATENT DOCUMENTS

| FR | 2 620 927 A1 | 3/1989 |
| FR | 2 663 528 A3 | 12/1991 |
| FR | 2 688 679 A1 | 9/1993 |
| FR | 2 914 173 A1 | 10/2008 |
| GB | 2 449 855 A1 | 12/2008 |

OTHER PUBLICATIONS

International Search Report, dated Jun. 20, 2011, from corresponding PCT application.

* cited by examiner

*Primary Examiner* — Daquan Zhao
(74) *Attorney, Agent, or Firm* — Im IP Law; C. Andrew Im

(57) ABSTRACT

A method for estimating a person's interpupillary distance (PD). Data is acquired by utilizing a predefined movement of the person in front of a camera. A morphological and dimensional parameters are calculated based on the acquired data.

7 Claims, 3 Drawing Sheets

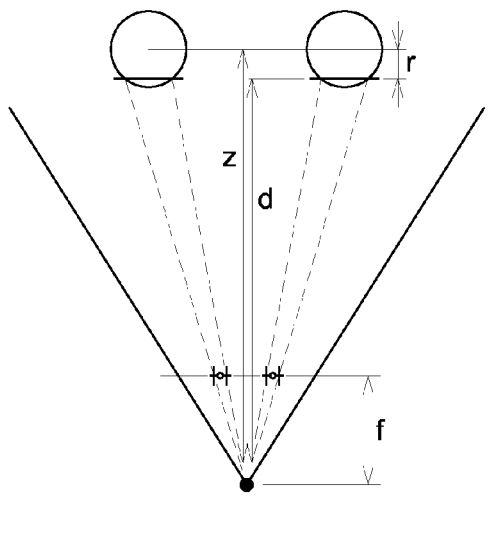
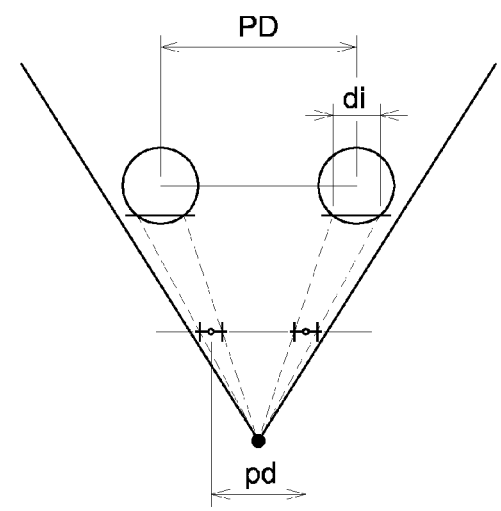
Fig. 3a  Fig. 3b
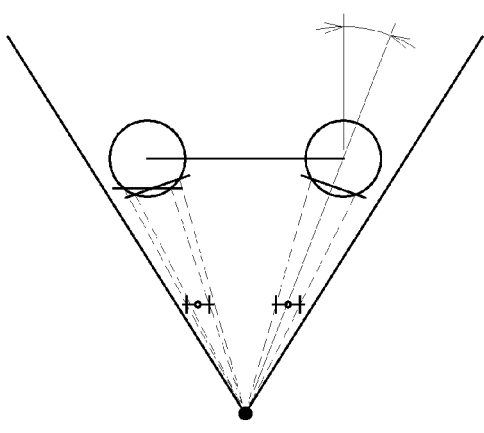
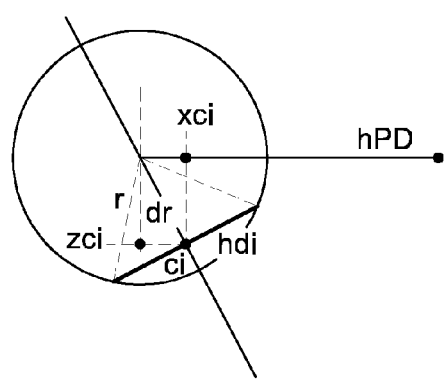
Fig. 4a  Fig. 4b

METHOD AND DEVICE FOR MEASURING AN INTERPUPILLARY DISTANCE

The present invention falls within the field of optics and more specifically of ophthalmology.

BACKGROUND OF THE INVENTION AND PROBLEM STATEMENT

When a person (hereafter called "subject") wishes to acquire spectacles, the first step is, naturally, to determine the characteristics of the lenses required for correcting their sight. This step is performed by an ophthalmologist. The next step is choosing a frame that matches the subject's wishes.

Lastly, the optician in charge of this person must take a series of measurements to adapt the spectacles (frame and lenses) to the subject's exact morphology, for actually manufacturing the spectacles fitted with the corrective lenses.

Among these measurements, it is clear that the interpupillary distance (called "PD" in the rest of the description for "Pupil Distance Measurement" or "PD Measurement") is a key measurement, which is defined as the distance separating the centers of the pupils of both eyes (see FIGS. 1 and 3b) when the subject is perfectly head on, with the head straight and looking to infinity. It is also called "PD far" to characterize the fact that the subject is looking to infinity. In addition, optical practitioners also use a close-look measurement ("PD near") and an intermediate measurement.

This interpupillary distance measurement PD effectively determines the relative distance between the optical axes of the lenses mounted in the spectacles. It is noted that each of these lenses is, in simplified fashion, geometrically conformed as the spaces comprised between two spherical caps having different centers.

Correct measurement of the interpupillary distance PD is the key to perfectly corrected vision. In contrast, incorrect measurement causes at least one of the lenses to be misaligned in relation to the optical axis of the eye located opposite the lens, resulting in imperfect vision and tired eyes.

The average distance between the centers of the pupils is 64 millimeters in adults, with 80% of the values falling between 62 and 68 mm. Accuracy of the order of 0.5 mm is required for correct vision, particularly for progressive lenses, which must be placed as accurately as possible in relation to the subject's eyes. It should be noted that with the gradual aging of the population, the proportion of progressive lenses in the total number of corrective lenses prescribed is increasing; it is currently over 20% of the total.

In general, the interpupillary distance measurement PD realized is the "PD far" performed with a pupilometer or by some other method. Thus, the supposed measurement is the distance between the lines going through the optical centers and the centers of the pupils and assumed to be parallel. This is based on four hypotheses: that the subject is truly looking to infinity; that the measurement instrument takes the orthographic projection into account; that it is sufficiently accurate; and that there is no vergency problem with the subject.

In practice, the expression of the PD distance takes the vergency of the subjects into account: for example, looking to infinity generally requires having the lines previously defined as divergent (non-parallel) because of the physical systems of the eye (cornea) and of perception (interior of the eye, brain).

In correlative fashion, two additional measurements are also desirable to determine the way the subject wears the spectacles, and the morphology of their face.

The first measurement is known as "mono-PD" and represents the distance between the center of the pupil and the center of the frame (which materializes the resting point of the spectacles on the nose) when the subject is looking to infinity.

The second measurement is called as "Fitting Cross Heights", which is used in the context of progressive lenses ("varifocals"). This measurement is the height of the line linking the two centers of the pupils in relation to a reference level of the spectacles (e.g. the bottom of the spectacles). As is also understood, accurate measurement of this height is preferable to ensure the spectacles are suitable for correct vision to infinity.

There are several conventional methods for performing the interpupillary distance PD measurement. The interpupillary distance measurement can be realized either between the two eyes (binocular measurement) or by calculating the distance between the center of one pupil and the center of the spectacles (monocular measurement).

One of the methods of the previous state of the art is simply to measure the space between the edges and irises of both eyes with a ruler while looking in a mirror. This approximative measurement yields an accuracy of the order of 3 millimeters, which is adequate for conventional corrective lenses, but not suitable for progressive lenses.

Another solution, generally used by opticians, consists of placing the subject's face on a fixed mechanical reference frame, which comprises, schematically, eyepieces and a thumbwheel, and performing an optical measurement. This method, which is more accurate than the previous one, nevertheless has inaccuracies: a single subject can be found to have interpupillary distances PD that differ by a few millimeters, depending on which optician performed the measurement.

Yet another method consists of taking at least one picture of the subject and of a calibration object and deducing the interpupillary distance PD from the value measured on the picture and from corrective coefficients determined according to the image of the calibration object. This method also has the drawback of requiring a predefined position of the subject, which is difficult to obtain in practice.

Opticians realize the "Fitting Cross Height" measurement more-or-less empirically by observing the subject wearing spectacles.

In addition, these measurements assume that the subject is effectively looking to infinity, which is rarely the case and which can also disrupt the measurement by one to two millimeters.

Lastly, it is known that the human eye is not a sphere and that its movement is not modeled by simple rotation, but by a combination of rotation and translation; this means that the measurement must take the orientation of the gaze into account at the time of said measurement, without which it cannot be extrapolated to the normal position of looking to infinity.

It is understood therefore that measurement is made difficult not only by existing equipment and methods, but by the very nature of the human body and by the unavoidable movements of or errors in positioning the subject.

In current optical systems, a simple carrying over of the distances is used. In the same way, when using a photographic optical system: a measurable offset can be seen, due to the perspective of the camera rather than to morphology. For a better measurement, the tridimensional position and morphology of the subject's visual system must be known. For measurement purposes, experts agree that the eye's center of rotation is the focal point where images are formed.

There are three-dimensional measurement systems, but these are very invasive and need to be implemented in stores with sophisticated and expensive equipment.

Objectives of the invention The objective of this invention is to propose a method for measuring the interpupillary distance that remedies the problems of inaccuracy and measurement difficulties mentioned above.

According to a second objective of the invention, the method can be implemented at lower cost, which means wider utilization can be envisaged.

A third objective of the invention is to provide an interpupillary distance measurement in a very short period of time.

Another objective of the invention is also to be implemented without requiring calibration objects.

The measurement method can be implemented with equipment that is generally available with consumers and uses a protocol that can be understood by anyone: this avoids every user needing to go to the store.

DESCRIPTION OF THE INVENTION

To achieve this, the invention concerns a method for estimating the interpupillary distance (PD) of a person, characterized in that it comprises:
- a data acquisition phase 100 that utilizes a predefined movement of the person in front of a camera; this data acquisition phase 100 comprises acquiring a set of successive images that represent the person's eyes, when the person's position changes from a first configuration of the face (position and/or orientation in relation to the camera) and a second configuration of the face.
- a morphological and dimensional parameter calculation phase 200 based on the acquired data.

According to various modes of implementation, possibly used together:

step 100 comprises the following steps:

step 101: place the person in front of the camera, at a previously chosen distance from the camera;

step 102: move the person's face towards the camera while looking straight at it;

step 103: stop when the person can no longer stare at the lens or receives a stop signal.

the distance previously chosen is substantially the length of an arm.

Step 102 can be replaced by other movements that allow eye movements to be distinguished from those of the face:

The person stares at the camera and turns their head from left to right.

The person keeps their head steady and looks towards different places.

The person looks at the camera, then to infinity.

The person looks at a set of predefined points on the screen.

step 200 comprises the following steps:

step 201: statistical measurements training;

step 202. characterize the image measurements;

step 203: determine statistically the 3D data and the parameters sought;

step 204: optimize the parameters non-linearly.

the parameters sought include the interpupillary distance PD, the diameter of the iris di, the camera's focal length f, the distances zi (i=1 ... n) between the camera and the person for the successive images captured during the movement.

step 201 comprises the following sub-steps:
  201a: measure a set of morphological and mechanical data,
  201b: construct a projection stage of the PD system described and build a correspondence table that samples the continuous reality of the parameters, depending on the following inputs and for given image sizes: PDpx, dipx, PD, di, f, z where PDpx and dipx are the image measurements of the data items PD and di,
  201c: establish several probability densities, smoothed by a kernel method and distributed into the tables that express the following functions, amongst others:
    i. PD=f (PDpx, dipx, f, zi)
    ii. di=f (PDpx, dipx, f, zi)

step 202 comprises the following sub-steps:
  202a: detect a face;
  202b: detect and recognize the eyes;
  202c: fine description of the irises by estimating the parameters of the circle or ellipse represented by the projection of the iris onto the image;
  202d: deduce the values PDpx, distance between the two centers of the images of the irises and dipx, the diameters of the images of the iris.

step 203 comprises the following sub-steps:
  203a: assuming the movement is at constant speed, express all the zi parameters, with two parameters: z0, the starting distance (the furthest) and dz, the distance between two image captures;
  203b: simulate a set of samplings of the movement to give the best probabilistic explanation of the parameters f, PD and di in relation to the measurements observed in the images PDpx and dipx.

sub-step 203b comprises the following points:
    i. for a set of realization triplets (z0, dz, f) such that the zi (i=1 ... n) and f are within a range of values acceptable for the protocol, a histogram is built of the triplets for which there are the most responses of (PD, di) pairs, utilizing the correspondence functions; the realizations of (zi, PDpx, dipx) are made to vary around the values under consideration so as to simulate the realization laws of the measurements;
    ii. the focal length f for the maximum peak of probabilities constructed is found;
    iii. from f, PD and di are deduced, using the same tables, such as the average of the normal asymptotic convergence properties of the experiments performed on the set of PD and di found;
    iv. the (z0, dz) pair for which the parameters above are most likely is found.

step 204 comprises the following sub-steps:
  204a: release the constant distance constraint between the zi values and initialize with the previous solution;
  204b: define the confidence levels for the 3D parameters by searching the set of values zi, PD, di, f that make it possible to minimize the reprojection error of the irises onto the acquired images.
  204c: utilization of a simplex Nelder-Mead-type algorithm or of an additive texture adjustment algorithm.

According to an advantageous implementation, the method comprises a phase 300 of calibrating the camera (estimating of its focal length f) used for acquiring the data;

said calibration comprises using a predefined object and presenting it in front of the camera at various distances and angular orientations; with said object comprising several concentric circles in a single plane, which makes it possible to calibrate a camera or two coplanar circles.

According to a preferred mode of implementation, the object is a compact disk (CD).

Advantageously, step 300 comprises the following substeps:

step 301: present and move the object in front of the camera;

step 302: estimate the center of the object;

step 303: detect the radial outline and obtain an image of the outlines with the main chained outlines of the image;

step 304: obtain a contour texture/map of distances to the contour of the object in front view;

step 305: use a texture alignment algorithm on the image of the contours to determine the calibration settings sought.

According to an advantageous implementation, the person moves while pressing an object of known size against their cheek, for example a coin.

This object makes it possible to set the sought values $z0$, $zi$ and $dz$.

When coupled with the first advantageous solution with camera calibration, this solution reduces the uncertainty over the accuracy of the measurement.

The invention also envisages a computer program product comprising program code instructions for executing a method as described when said program is run on a computer.

The invention envisages in another aspect a device for measuring an estimate of the interpupillary distance (PD) of a person comprising:

means of acquiring data during a predefined movement of the person in front of a camera;

means of calculating morphological and dimensional parameter based on the acquired data.

BRIEF DESCRIPTION OF THE FIGURES

The description that follows, given solely as an example of an embodiment of the invention, is made with reference to the figures included in an appendix, in which:

FIGS. 3a and 3b illustrate the parameters, including the interpupillary distance, that are to be measured in the case of a movement by the user towards the camera while looking to infinity, FIG. 1a before the movement and FIG. 1b after this movement;

FIG. 4a illustrates in similar fashion the location of the eyes at the end of the user's movement towards the camera by fixing it and FIG. 4b is a detail of an eye and of the associated measurement parameters;

DETAILED DESCRIPTION OF AN EMBODIMENT OF THE INVENTION

The method according to the invention is designed to be implemented in the form of a computer program comprising a series of program code instruction lines to execute the steps of the method when said program is executed on a computer.

The computer in question is for example a PC-type microcomputer.

Figure 1:
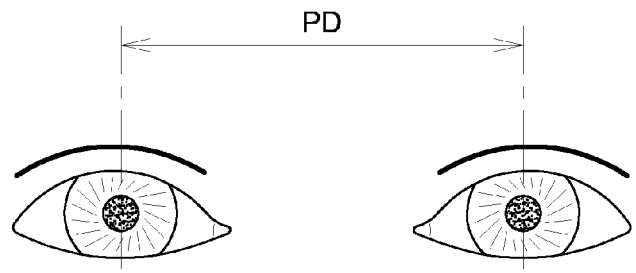
FIG. 1 illustrates the interpupillary distance that is to be measured.
Figure 2:
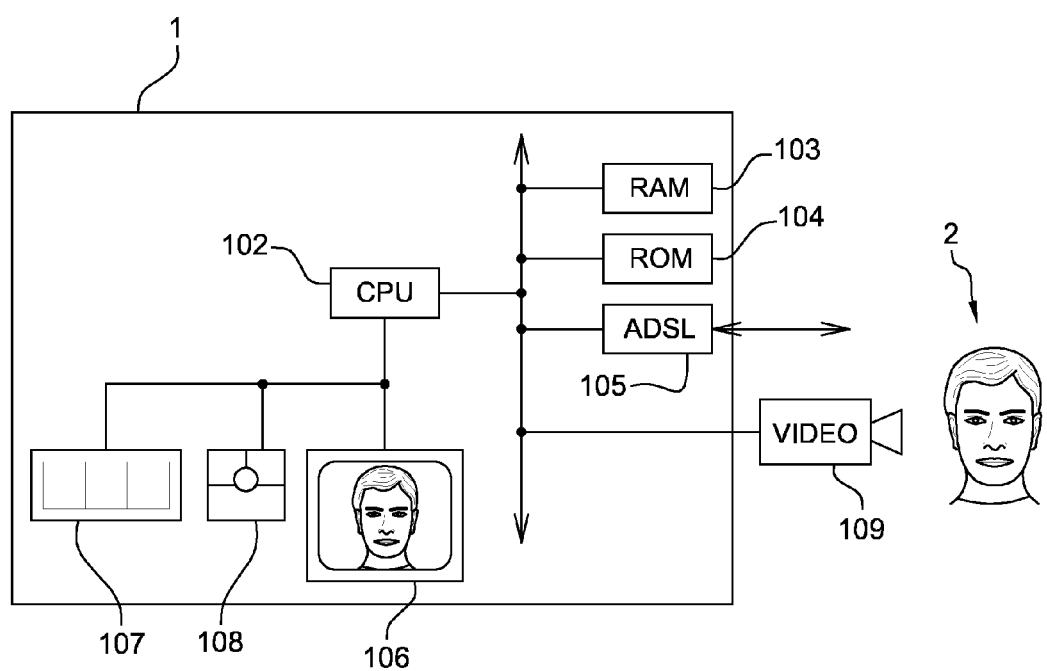
FIG. 2 schematically illustrates the elements implemented in the method according to the invention.

As can be seen in FIG. 2, the measuring device that implements the method according to the invention therefore comprises a micro-computer 1, used by an operator 2, who is, in this non-limiting example, the same as the subject of the interpupillary distance measurement; said micro-computer comprises, for example, the following connected to each other by an address and data bus 101:

a central processing unit 102;
RAM memory 103;
ROM memory 104;
a network interface 105, e.g. a conventional ADSL modem;

and, separate from the bus 101:

a visualization screen 106;
a keyboard 107;
a mouse 108.

The RAM memory 103 provides a means of storing information, which can be read by a computer or a microprocessor. It stores data elements, variables and intermediate processing results.

The ROM memory 104 provides a means of storing information, which can be read by a computer or a microprocessor. It stores instructions of a computer program that makes up the implementation of the method, which is the subject of the invention, possible.

According to a variant, the read-only memory 104 is partially or totally removable and comprises, for example a CD-ROM.

The device also comprises a still-image capture device, e.g. a video camera 109 of conventional type, connected to the computer 1 by the data by the data bus 101.

Each of the elements illustrated in FIG. 2 is well known to experts. These elements will therefore not be described here.

The central processing unit 102, located on the operator's premises, is designed to implement the flowcharts described below.

Calculation Model and Device

The invention, such as described here in a non-limiting example of implementation, comprises an image capture system and an associated protocol. They make it possible to estimate the interpupillary distance of a person with verified accuracy and quality equal to that of conventional measurement instruments (typically<1 mm). In addition, they make it possible to determine the parameters of the camera and the distances at which the person is located when the images are captured by the camera.

For this, the following eye-iris system illustrated in FIGS. 3a and 3b and parameterized with the following variables is considered:

r: radius of the ocular globe
di: iris diameter, hdi: iris radius
PD: interpupillary distance, hPD: half-distance between the eyes
z: distance from the center of the eyes to the camera
d: distance from the center of the irises to the camera
f: focal length of the camera The overall image capture system comprises:
a computer
a screen
at least one video camera (e.g. "webcam" type) or a camera possibly located above the screen.

The user places themselves centered, such that they are filmed by the camera and see their own front view in the image recorded by the camera and repeated onto the screen.

For this system, the position, shape and size of the irises thus projected can be measured.

To find these parameters, a set of information items called "prior knowledge" can be used favorably. These include, for example:
1. limited uncertainty on the morphological parameters:
   PD: sigma_PD
   di: sigma_di
   r sigma_r
2. movement verified
3. focal length determined
   by a calibration method described below
   by knowledge of the manufacturing techniques Solutions are proposed each time prior knowledge of type 1, 2 or 3 is added, with increased accuracy.

Using a predefined movement by the user makes it possible to capture several images to determine which parameters are unchanging in the image captures. At each image capture, a new distance zi is to be estimated.

The user is asked to move according to the following movement:
1. move towards (or away from) the camera while looking to infinity:
   a. the irises can be considered to be in a single plane
   b. they can be accurately identified according to an AAM [Cootes98] type method for example.
   c. The camera is calibrated using a method, described below, that allows two circles on a single plane—the irises—to be considered and to measure the deformation of their projection into ellipses depending on their position and on the focal length.
   d. The focal length f can then be estimated from the appearance of the irises.

In an implementation variant, possibly used in combination with the previous one, the method uses the following user movement protocol:
2. move towards (or away from) the camera while staring at said camera's lens:
   a. the eyes turn by an angle that depends on the distance to the camera. In practice, the projection of the irises can almost always be assimilated to a circle.
   b. This projective invariance of the movement within the image allows the fact that the model's appearance essentially depends on the pair (PD/di) whatever the compensation of values f and z may be.

FIGS. 4a and 4b show the new parameters used in this case.

In both movement cases, the requirement for estimating the system's 3D positioning parameters tx, ty, rx, ry is removed in the first instance.

Calculation Method

Figure 5:
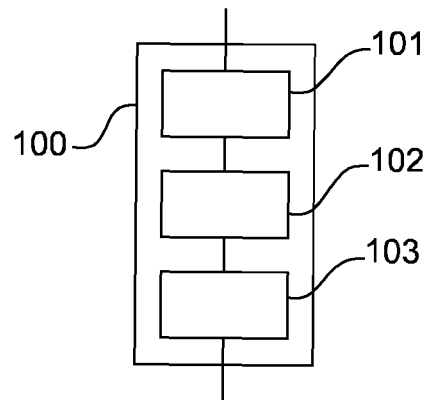
FIG. 5 illustrates the steps of the data acquisition phase of the measurement method that complies with a mode of implementation of the invention.

Firstly, the method comprises an image capture phase 100 (see FIG. 5), which uses a predefined movement by the user (moving towards or away from the camera):

step 101. The user positions themselves at an arm's length distance from the camera;

step 102. The user moves their face towards the camera at constant speed while staring at it;

step 103. The user stops when they can no longer stare at the lens or when the system signals them to stop.

Figure 6:
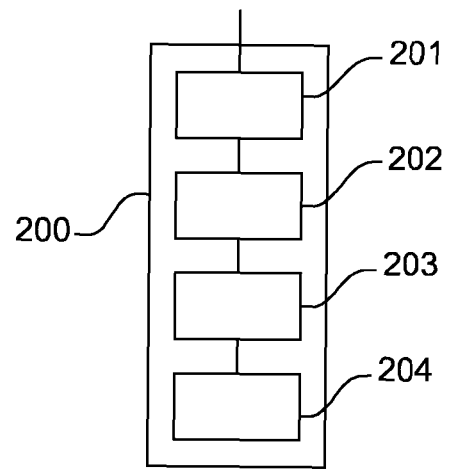
FIG. 6 illustrates the steps of the calculation phase of the measurement method that complies with a mode of implementation of the invention.

The parameters sought are estimated in a calculation phase 200 (see FIG. 6), according to the following diagram:

step 201. Statistical measurement training

201a. Measurement of a set of morphological PD, di, r and mechanical data: f

201b. Construct a projection stage of the PD system described and build a correspondence table that samples the continuous reality of the parameters, depending on the following inputs and for given image sizes: PDpx, dipx, PD, di, f, z where PDpx and dipx are the image measurements of the data items PD and di.

201c. Establish several probability densities, smoothed by a kernel method and distributed into the tables that express the following functions, amongst others:
   i. PD=f (PDpx, dipx, f, zi)
   ii. di=f (PDpx, dipx, f, zi)

step 202. Characterize the image measurements;

202a. Face detection, for example using the Viola and Jones algorithm, which is known in itself and will not be detailed here.

202b. Detect and recognize the eyes, for example with an AAM-type model [Cootes98]:

202c. Fine description of the irises by estimating the parameters of the circle or ellipse represented by the projection of the iris onto the image;

202d. Deduction (at sub-pixel level, i.e. better than the value of a pixel, using the parametric estimation of the iris images) of the values PDpx, the distance between the two centers of the iris images, and dipx, the diameters of the images of the irises.

step 203. Statistical determination of the 3D data, parameters looked for: PD, di, f, zi (i=1 . . . n).

203a. Assuming the movement is at constant speed, the set of parameters zi will be expressed with two parameters: z0, the starting distance (the furthest) and dz, the distance between two image captures. These two parameters completely define the set of zi values for image captures. The zi values represent a sampling of the movement. One of the objectives of the algorithm is to determine them.

203b. A set of samplings of the movement is simulated to give the best probabilistic explanation of the parameters f, PD and di in relation to the measurements observed in the images PDpx and dipx.
   i. For a set of realization triplets (z0, dz, f) such that the values zi (i=1 . . . n) and f are within a range of values acceptable for the protocol, a histogram is established of the triplets for which there are the most responses of (PD, di) pairs, utilizing the correspondence functions. The realizations of (zi, PDpx, dipx) are made to vary around the values under consideration so as to simulate the realization laws of the measurements.
   ii. The focal length f for the maximum peak of probabilities constructed is found;
   iii. PD and di are deduced based on f, using the same tables, such as the average of the normal asymptotic convergence properties of the experiments performed on the set of PD and di found;
   iv. The (z0, dz) pair for which the parameters above are most likely is found.

step 204. Non-linear optimization of the parameters

204a. The constraints of constant distance between the zi are removed. Initialize with the previous solution.

204b. Define confidence levels for the 3D parameters. The set of zi, PD, di, f values is sought that allows the reprojection errors of the irises on the captured images to be minimized.

204c. A simplex algorithm, e.g. Nelder-Mead-type, or an additive texture adjustment algorithm is used.

Lastly the following are obtained: the values of morphological and dimensional parameters that define the interpupillary distance PD; the camera's focal length f; the distance from the user to the camera; and the relative position of their eyes in relation to this camera. In particular, the method makes it possible to determine the user's interpupillary distance with a verified accuracy equal to that of conventional measurement instruments (typically an error of less than one millimeter).

These last allow, in particular, placing an image of a virtual model of spectacles on the image of the user's face, captured by the camera. The method guarantees the appearance of the ratios between the sizes of the user's face and of the spectacles in the image. The method makes it possible to insert digital 3D models of spectacles coming from real objects in the scene, at the exact distance required to allow a metrically correct fitting for any photo, irrespective of the position of the face in front of the camera.

Similarly, the exact measurement of the interpupillary distance makes it possible to manufacture spectacles suitable for wearing by the user and whose lenses are positioned optically in front of the user's eyes.

To summarize, the method that is the subject of this application measures the interpupillary distance in three dimensions PD 3D and the mono PD distance PD 3D independently of the image capture system.

In effect, with this method, the metric distance is measured between the 3D positions of the focal points rather than the arbitrary projections used in current systems.

Using this method, it is possible to find all the conventional PD measurements (i.e. PD "near" and PD "far"), as well as the vergency model specific to each subject. This is useful for constructing and mounting lenses that are suited to the eye's travel, rather than to a single or a finite number of directions of sight. This measurement of PD 3D is therefore more relevant for mounting the lenses and for the accuracy of cutting out the lenses than are conventional PD measurements.

Variants of the Invention

The scope of this invention is not limited to the details of the embodiments considered above as an example, but on the contrary extends to modifications in the reach of the expert.

In an implementation variant, the calibration of the camera is performed by using a compact disk (CD) type of object and presenting it in front of the camera at various distances and angular orientations.

Below, "Camera calibration" means estimating its focal length f. The other parameters of the stenopeic model are deemed satisfactorily known for the application. For example, the sensor in most modern digital cameras consists of square pixels and the optical center can reasonably be set at the center of the sensor (i.e. of the image).

Here, this calibration is based on results known to experts, including notably:
An object comprising several concentric circles on a single plane makes it possible to calibrate a camera
Two coplanar circles make it possible to calibrate a camera These principles are then applied; an object that everyone has is chosen, such as e.g. a CD or a coin, which comprises concentric circles.

Two approaches are proposed:
Algebraic solution: this uses geometric properties to obtain an algebraic result. It validates theoretical aspects.
3D alignment solution: this uses a 3D modelization of the system. A 3D alignment process is used that allows the camera to be calibrated whatever the known 3D object may be, provided that it has a plane on which certain dimensions are known.

This latter approach is very robust: it makes it possible to function in many lighting conditions and has low sensitivity to obscuration. It makes it possible to find all the 3D parameters of the scene: position and orientation of the object, camera parameters (focal length in particular).

Figure 7:
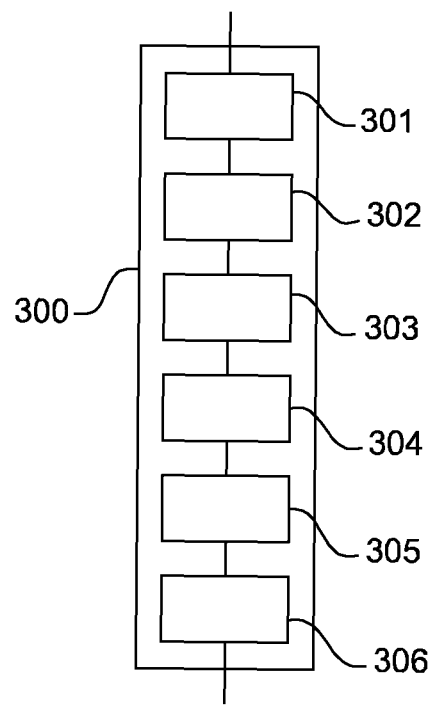
FIG. 7 illustrates the steps of a camera calibration phase used in a variant of the method.

The description that follows concerns a camera calibration phase 300 that implements an approach with a CD. It comprises the following steps (see FIG. 7):
step 301: present and move the CD in front of the camera;
step 302: estimate the center of the CD: user click or detection of the hand;
step 303: detect a radial outline, for example with a method using a Canny-Deriche filter. An outline image is obtained with the image's main chained outlines;
step 304: obtain a contour texture/map of distances to the contour of the object in front view;

The homography that links the texture and the CD oriented and positioned in the 3D scene can be expressed.
step 305: use a texture alignment algorithm on the image of the contours to determine the calibration settings sought.

To obtain the initial solution to this algorithm, either the algebraic method or a set of linear estimates can be used in a step 306 by setting certain parameters.

An additive texture adjustment algorithm can be used in the context of step 204c, described above.

In implementation variants, possibly used together with the method described above, other prior knowledge is utilized:
Focal length f: "prior knowledge" of the camera's parameters (focal length f) can be obtained by ascertaining the model of camera used. For each known camera, a calibration has been performed beforehand, for example by using the method described above, and stored. If the camera is unknown, the calibration is performed as described above.
zi distance: the user moves towards the camera with a coin placed on their face in the vicinity of their eye, substantially in the plane of their eyes.
Arm length: The user can be asked to place themselves an arm's length away from the camera. Using the statistical morphological data, by knowing the gender and size of the person, the average length of their arm can be deduced. This allows the value of the first zi distance to be given.

Other protocols can also be envisaged in variants.

The parameters f, PD and z of the eyes can be determined from a single forward-facing photograph of a person holding a CD, one extremity of which is pressed up against the edge of their eye.

This protocol does not constitute a simple carrying over of the CD's image measurements, some distances of which are known, but comprises the following operations:
Estimate f using the detection of the different ellipses, which are the projections of the edges of the CD.
Estimate the plane of f and the depth z of the point of contact f with the face.

In yet another variant, two video cameras, e.g. of webcam-type, are used and the image obtained from the two sources are used by the otherwise-unchanged method. This variant makes it possible to save time in acquiring the parameters of the face. It makes it possible to calculate the movement actually traveled dz between the views and therefore provides a higher level of accuracy in the estimation.

It is clear that the method could be applied to the placement of an image of another object of known dimensions on the user's face, provided its distance from the camera and the main dimensions of their face, as determined by a method such as described above, are known.

It should be noted that the proposed invention is not limited to carrying over the measurements of a known object onto image measurements to be performed, contrary to the other optical methods. This actually is a 3D metric estimation of the parameters sought in the subject's real space.

Once the 3D PD measurement is known, it is possible to find the "conventional" PD measurements via an additional protocol. Indeed, by using a single additional photo of the subject looking at infinity, in which the eyes are visible, a 3D adjustment of the face/eyes system on the image makes it possible to find the subject's own vergency to infinity and to deduce the PD "far" value therefrom.

Similarly, if the subject is looking to a defined distance, the value of PD for this distance can be calculated (so the PD "near" can be deduced). The corollary of this result is the expression of a model of the vergency of each eye whose samples are the number of captures at different distances.

In the method described previously, the training measurements are generated using 3D data. Therefore it is 3D metric data that is found. Another way to proceed, described below, rebuilds the complete ocular globes/face/iris 3D system from the image measurements performed.

3D rebuilding and interpupillary distance PD measurement system.

In this protocol, the centers of rotation of the ocular globes are found. These centers represent the vision centers around which the eyes turn and which are the optical center of the eye system. The interpupillary distance PD 3D is defined as the 3D metric measurement between the two centers of rotation. At the same time, all the 3D parameters of the scene are retrieved. This protocol assumes that the work is carried out knowing only the value of the camera's focal length and the depth z of the face or some main dimensions of the face. These values can be obtained by calibration or assumed.

The principle is as follows:

From the n images captured, the following set of image indices are retrieved by detection or 2D tracking:

1. Points of interest of the face that make it possible to obtain the face's rigid movement.

2. Contours of the irises that make it possible to obtain the overall movement to which the ocular globes are subjected (rigid movement of the face+rotations of the ocular globes).

3. Points or outlines that describe the ocular globes/face border (such as, e.g. the commissures of the eyes or the outlines of the eyelids on the ocular globes). These points or outlines, which are only subject to the rigid movement of the face and which link the face to the ocular globes make it possible to de-correlate the rigid movement from the ocular globes and therefore to reconstruct in the real space the 3D curves of the rotational movement of the globes (their trajectory).

The image indices are matched and represent a sought set of 3D points or 3D curves.

The 3D coordinates of each eye's Ol and Or centers of rotation are sought.

Let n be the number of images captured and i the number of the current image.

Let m be the number of points of interest on the face and i the index of the current point.

Let $Pv\_j$ be the 3D point of interest looked for and $pv\_ij$ its associated image index (projection).

Let p be the number of points of interest that describe the globes/face border and k the index of the current point.

Let $Pe\text{-}k$ be the 3D point of interest that describes the globes/face border and $pe\_ik$ its associated image index.

Let q be the number of outline points of the iris and l the index of the current point.

Let $Pg\_l$ be the point outline of the iris and $pg\_il$ its associated image index.

The following are looked for:

the rigid movement (Rx, Ry, Rz, Tx, Ty, Tz) to which the points Pv and Pe are subjected.

The combined movement (rigid movement of the face+rotation of the globes) to which the ocular globes and the points Pg are subjected.

the positions of the centers of rotation Ol(x,y,z) and Or(x,y,z), such that the projection of the point Cil (respectively Cir) (the 3D center of the iris at a distance dr from Ol respectively Or) that follows the rotation of the eye Re(Rex, Rey, Rez) is the closest of the matching image indices.

This system is resolved by using a least squares minimization between the projection if the 3D points/curves sought ($Pv\_j$, $Pe\_k$ and $Pg\_l$) and the image indices. This resolution by least squares is a method known to experts and commonly called "bundle adjustment". The initial solution can be defined using the prior knowledge of the scene, such as the statistical data on the eye and face (size of the ocular globes, irises, etc.)

The invention claimed is:

1. A method for determining a fitting position of an optical axis of lenses mounted in spectacles of a person to the position of the person's eyes, comprising the steps of:
    determining an interpupillary distance (PD) of the person by a processor, the interpupillary distance (PD) determines a relative distance between the optical axis, the processor is configured to:
        acquire data by capturing a set of successive images, using a predefined movement of the person in front of a camera, representative of the person's eyes during the predefined movement from a first configuration of a face of the person to a second configuration of the face of the person; and
        calculate morphological and dimensional parameters based on the acquired data;
    determining the fitting position of the optical axis of lenses to the determined interpupillary distance;
    wherein the processor is configured to calculate the morphological and dimensional parameters by:
        measuring a set of morphological parameters PD, di, r and mechanical parameter f, where di is an iris diameter, r is a radius of an ocular globe and f is a focal length of the camera;
        constructing a projection stage of a PD system and generating a correspondence table that samples a continuous reality of the morphological and dimensional parameters, depending on the following inputs for given image sizes: PDpx, dipx, PD, di, f, z where z is a distance from a center of the person's eyes to the camera, and where PDpx and dipx are image measurements of the data PD and di;
        establishing a plurality of probability densities, smoothed by a kernel method and distributed into the correspondence table that express at least the following functions: PD=f (PDpx, dipx, f, zi) and di=f (PDpx, dipx, f, zi), where zi (i=1 ... n) are distances between the camera and the persons for the successive images acquired during the predefined movement, and n is the number of images;

characterizing the image measurements by detecting a face of the person; detecting and recognizing the person's eyes; descripting irises by parameters of a circle or ellipse represented by a projection of each iris onto an image; and determining values PDpx, a distance between two centers of the images of the irises and dipx, and diameters of the images of said each iris;

determining statistically the morphological and dimensional parameters PD, di, f and zi (i=1 ... n) by expressing all the zi parameters, with two parameters: a starting distance z0 and a distance between two image captures dz; and simulating a set of samplings of the predefined movement to provide a probabilistic determination of the parameters f, PD and di in relation to the measurements PDpx and dipx observed in the images to determine statistically the morphological and dimensional parameters; and optimizing the morphological and dimensional parameters non-linearly using a simplex algorithm or an additive texture adjustment algorithm by releasing a constant distance constraint between the zi values and initializing with a previous solution; and defining confidence levels for 3D parameters by searching the set of zi, PD, di, f values to minimize a re-projection error of the irises onto acquired images.

2. The method according to claim 1, wherein the predefined movement of the person comprises placing the person in front of the camera, at a predetermined distance from the camera; moving the person's face towards the camera while the person is looking straight at the camera until the person can no longer stare at the lens or receives a stop signal; and wherein the predetermined distance is a length of the person's arm.

3. The method according to claim 1, wherein the step of simulating the set of samplings of the predefined movement comprises the steps of:

for a set of realization triplets (z0, dz, f) such that the zi (i=1 ... n) and f are within a range of values acceptable for a protocol, building a histogram of the triplets, for which there are maximum responses of (PD, di) pairs, utilizing correspondence functions, and varying realizations of (zi, PDpx, dipx) around values under consideration to simulate realization laws of the measurements;

determining the focal length f for a maximum peak of probabilities constructed;

determining average of normal asymptotic convergence properties of the set of PD and di found from f, PD and di using the correspondence table; and determining a (z0, dz) pair for which the parameters f, PD and di.

4. The method according to claim 1, further comprising the step of calibrating the camera to determine the focal length f used for acquiring the data by presenting a predefined object in front of the camera at various distances and angular orientations, the predefined object comprising a plurality of concentric circles in a single plane to calibrate the camera with two coplanar circles.

5. The method according to claim 4, wherein the object is a compact disk (CD).

6. The method according to claim 4, further comprising the steps:

presenting and moving the predefined object in front of the camera;

determining a center of the predefined object;

detecting radial outlines and obtaining an image of the radial outlines with main chained outlines of the image;

determining a contour texture or map of distances to contours of the predefined object in a front view;

determining calibration settings using a texture alignment algorithm on an image of the contours.

7. A non-transitory computer program product storing program code instructions for executing a method according to claim 1 when said program is run on a computer.

* * * * *